(12) United States Patent
Gu et al.

(10) Patent No.: US 11,188,819 B2
(45) Date of Patent: Nov. 30, 2021

(54) ENTITY MODEL ESTABLISHMENT

(71) Applicant: INTERNATIONAL BUSINESS MACHINES CORPORATION, Armonk, NY (US)

(72) Inventors: Yu Gu, Austin, TX (US); Dingcheng Li, Sunnyvale, CA (US); Kai Liu, Malden, MA (US); Su Liu, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 886 days.

(21) Appl. No.: 15/591,235

(22) Filed: May 10, 2017

(65) Prior Publication Data
US 2018/0330231 A1 Nov. 15, 2018

(51) Int. Cl.
*G06N 3/08* (2006.01)
*G06N 5/04* (2006.01)
(Continued)

(52) U.S. Cl.
CPC .......... *G06N 3/08* (2013.01); *G06F 16/3344* (2019.01); *G06F 40/284* (2020.01); *G06F 40/295* (2020.01); *G06F 40/30* (2020.01); *G06N 3/0454* (2013.01); *G06N 5/022* (2013.01); *G06N 5/041* (2013.01); *G16H 10/20* (2018.01);
(Continued)

(58) Field of Classification Search
CPC ........ G06N 3/08; G06N 3/0454; G06N 5/022; G06N 5/041; G06N 7/005; G16H 40/67; G16H 50/50; G16H 10/60; G16H 30/20; G16H 50/20; G16H 10/20; G06F 16/3344; G06F 40/284; G06F 40/295; G06F 40/30; G06F 2111/10
See application file for complete search history.

(56) References Cited

U.S. PATENT DOCUMENTS 6,185,592 B1 2/2001 Boguraev
6,438,543 B1 8/2002 Kazi
(Continued)

FOREIGN PATENT DOCUMENTS

CN 102262632 11/2011
CN 103268348 A 8/2013
(Continued)

OTHER PUBLICATIONS

Liu, Sijia, et al. "An Infinite Mixture Model for Coreference Resolution in Clinical Notes." AMIA Summits on Translational Science Proceedings 2016 (2016): 428. (Year: 2016).*
(Continued)

*Primary Examiner* — Luis A Sitiriche
*Assistant Examiner* — Sehwan Kim
(74) *Attorney, Agent, or Firm* — L. Jeffrey Kelly

(57) ABSTRACT

Disclosed aspects relate to entity model establishment using an infinite mixture topic modeling (IMTM) technique. A set of event data which corresponds to a set of events may be detected. Using the IMTM technique, the set of event data which corresponds to the set of events may be analyzed. Based on analyzing the set of event data using the IMTM technique, a set of entity models for the set of events may be determined. Based on the set of entity models for the set of events, a subset of the set of entity models for the set of events may be established.

19 Claims, 11 Drawing Sheets

(51) Int. Cl.
| | |
|---|---|
| *G06N 3/04* | (2006.01) |
| *G06N 5/02* | (2006.01) |
| *G06N 7/00* | (2006.01) |
| *G16H 50/50* | (2018.01) |
| *G16H 10/60* | (2018.01) |
| *G06F 16/33* | (2019.01) |
| *G16H 50/20* | (2018.01) |
| *G16H 30/20* | (2018.01) |
| *G16H 10/20* | (2018.01) |
| *G16H 40/67* | (2018.01) |
| *G06F 40/30* | (2020.01) |
| *G06F 40/284* | (2020.01) |
| *G06F 40/295* | (2020.01) |
| *G06F 111/10* | (2020.01) |

(52) U.S. Cl.
CPC ............. *G16H 10/60* (2018.01); *G16H 30/20* (2018.01); *G16H 40/67* (2018.01); *G16H 50/20* (2018.01); *G16H 50/50* (2018.01); *G06F 2111/10* (2020.01); *G06N 7/005* (2013.01)

(56) References Cited

U.S. PATENT DOCUMENTS

| | | | |
|---|---|---|---|
| 8,457,950 | B1 | 6/2013 | Gardner |
| 8,862,460 | B2 | 10/2014 | Cai |
| 9,311,301 | B1 | 4/2016 | Balluru et al. |
| 9,535,902 | B1 | 1/2017 | Michalak |
| 9,582,482 | B1* | 2/2017 | Sharifi ............... G06F 9/451 |
| 9,633,002 | B1 | 4/2017 | Balluru et al. |
| 2009/0076799 | A1 | 3/2009 | Crouch |
| 2010/0293195 | A1* | 11/2010 | Houghton ......... G06F 16/285 707/776 |
| 2011/0106807 | A1 | 5/2011 | Srihari |
| 2015/0112664 | A1 | 4/2015 | Srinivasan |
| 2015/0278200 | A1 | 10/2015 | He |
| 2016/0378855 | A1 | 12/2016 | Roberts |
| 2017/0330106 | A1* | 11/2017 | Lindsley ............ G06N 5/043 |
| 2018/0330231 | A1 | 11/2018 | Gu |

FOREIGN PATENT DOCUMENTS

| | | |
|---|---|---|
| CN | 110612522 A | 12/2019 |
| DE | 112017007530 T5 | 1/2020 |
| GB | 2576659 A | 2/2020 |
| WO | 2018207013 A1 | 11/2018 |

OTHER PUBLICATIONS

Heinrich, Gregor. Parameter estimation for text analysis. Technical report, 2005. (Year: 2005).*

Dong, Li, et al. "Question answering overfreebase with multi-column convolutional neural networks." Proceedings of the 53rd Annual Meeting of the Association for Computational Linguistics and the 7th International Joint Conference on Natural Language Processing (vol. 1: Long Papers). 2015. (Year: 2015).*

Collobert, Ronan, et al. "Natural language processing (almost) from scratch." Journal of machine learning research Aug. 12, 2011: 2493-2537. (Year: 2011).*

Liu, Sijia, et al. "An Infinite Mixture Model for Coreference Resolution in Clinical Notes." AMIA Summits on Translational Science Proceedings 2016 (2016): 428. (Year: 2016).*

Heinrich, Gregor. Parameter estimation for text analysis. Technical report, 2005. (Year: 2005).*

Dong, Li, et al. "Question answering over freebase with multi-column convolutional neural networks." Proceedings of the 53rd Annual Meeting of the Association for Computational Linguistics and the 7th International Joint Conference on Natural Language Processing (vol. 1: Long Papers). 2015. (Year: 2015).*

Collobert, Ronan, et al. "Natural language processing (almost) from scratch." Journal of machine learning research Aug. 12, 2011: 2493-2537. (Year: 2011).*

Wan, Li, Leo Zhu, and Rob Fergus. "A hybrid neural network-latent topic model." Artificial Intelligence and Statistics. PMLR, 2012. (Year: 2012).*

Mei, Qiaozhu, et al. "Topic modeling with network regularization." Proceedings of the 17th international conference on World Wide Web. 2008. (Year: 2008).*

Liu et al., "An Infinite Mixture Model for Coreference Resolution in Clinical Notes", Proceedings—AMIA Joint Summits on Translational Science, Published online Jul. 22, 2016, pp. 428-437, PMCID: PMC5009297.

Wikipedia, "Fast Healthcare Interoperability Resources", printed on Sep. 17, 2018, 4 pages, https://en.wikipedia.org/wiki/Fast_Healthcare_Interoperability_Resources.

Wikipedia, "Chinese restaurant process", printed on Sep. 17, 2018, 5 pages, https://en.wikipedia.org/wiki/Chinese_restaurant_process.

International Search Report, International Application No. PCT/IB2017/057985, International Filing Date: Dec. 15, 2017, dated Apr. 16, 2018, 9 pages.

Liu et al., "An Infinite Mixture Model for Coreference Resolution in Clinical Notes," AMIA Joint Summits Translational Science Proceedings, 2016; 2016, Published online Jul. 22, 2016. PMCID: PMC5009297. pp. 428-437.

JP Office Action, Japanese Patent Application No. 2019-561140, English Translation, Date of Drafting: Aug. 5, 2021, 25 pages.

Liu et al., "An Infinite Mixture Model for Coreference Resolution in Clinical Notes", Proceedings of AMIA Joint Summits on Translational Science, American Medical Informatics Association, Jul. 22, 2016, pp. 428-437.

* cited by examiner

800

$$P(m_i = e_j | M_{-i}, \alpha) = \begin{cases} \dfrac{\sum e_j}{i-1+\alpha} & \text{if } e_j \leq K \\ \dfrac{\alpha}{i-1+\alpha} & \text{if } e_j > K \end{cases}$$

ENTITY MODEL ESTABLISHMENT

BACKGROUND

This disclosure relates generally to computer systems and, more particularly, relates to named entity recognition (NER) and entity relation detection (ERD) model establishment using an infinite mixture topic modeling (IMTM) technique. Management of data may be desired to be performed as efficiently as possible. As data needing to be managed increases, the need for NER and ERD establishment using an IMTM technique may also increase. More specifically, NER and ERD systems may have various challenges as described herein.

Natural language processing is useful to process electronic health records (EHRs). However, poor performance in relation detection tasks, such as coreference (linguistic expressions pertaining to the same entity/event) may affect the quality of EHR processing. Hence, there is a need to advance relation detection from EHRs. Many clinical coreference resolution systems are based on either supervised machine learning or rule-based methods. The need for manually annotated corpus hampers the use of such system in large scale.

Cognitive computing may be used to facilitate dynamic clinical decision support. Multiple challenges may exist in clinical decision support, cohort identification, or patient risk prediction and analysis. In particular, current clinical/medical identical NER and ERD systems have problems which may be addressed. Supervised models, such as pairwise classification, both strongly depend on annotated corpus which includes less portability and may include difficult to catch global information which can lead to an uninformed decision. Rule based deterministic systems, like the multipass sieve require well-crafted features or rule generations. Unsupervised models, like, pure Bayesian framework includes randomness which reduces the result consistency and mostly rely on co-occurrences.

SUMMARY

Aspects of the disclosure relate to NER and ERD in free texts using an infinite mixture topic modeling (IMTM) technique with a neural network. The IMTM technique can construct entity chains among medical events and a neural entity pair refiner (NEPR) technique to improve performance. In embodiments, the entity chain may include identical entity chains. Features may consider uncertainty of entity data in each document. The dynamicity of the IMTM technique in generating new entities may have positive impacts with respect to the need of pre-estimation of entity numbers. In embodiments, traceable longitudinal electronic health records facilitated by the NER and ERD may be constructed. Aspects related to a semi-supervised feature may have positive impacts with respect to a level of dependency on training data.

Disclosed aspects relate to entity model establishment using an infinite mixture topic modeling (IMTM) technique. A set of event data which corresponds to a set of events may be detected. Using the IMTM technique, the set of event data which corresponds to the set of events may be analyzed. Based on analyzing the set of event data using the IMTM technique, a set of entity models for the set of events may be determined. Based on the set of entity models for the set of events, a subset of the set of entity models for the set of events may be established. Altogether, aspects of the disclosure can have performance or efficiency benefits. Aspects may save resources such as bandwidth, disk, processing, or memory.

In embodiments, the set of event data which corresponds to the set of events is ingested using the IMTM technique. A certain group of mention elements of the set of event data may be processed using the IMTM technique. As such, a respective mention element of the certain group of mention elements may correlate to one or more distinct entity elements. In various embodiments, the set of event data which corresponds to the set of events may be clustered using a similarity metric and based on analyzing the set of event data using the IMTM technique. In certain embodiments, a set of IMTM parameters may be derived for utilization by the IMTM technique using a Gibbs sampling technique with respect to the set of event data.

In embodiments, the set of entity models for the set of events may be analyzed using a neural entity pair refining (NEPR) technique. Based on analyzing the set of entity models using the NEPR technique, the subset of the set of entity models for the set of events can be determined. In various embodiments, a set of features may be extracted using a natural language processing technique. The set of features can both be indicated by the set of entity models and be derived from the set of event data. Using the IMTM technique in combination with the NEPR technique may provide various performance or efficiency benefits.

The above summary is not intended to describe each illustrated embodiment or every implementation of the present disclosure.

BRIEF DESCRIPTION OF THE SEVERAL VIEWS OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
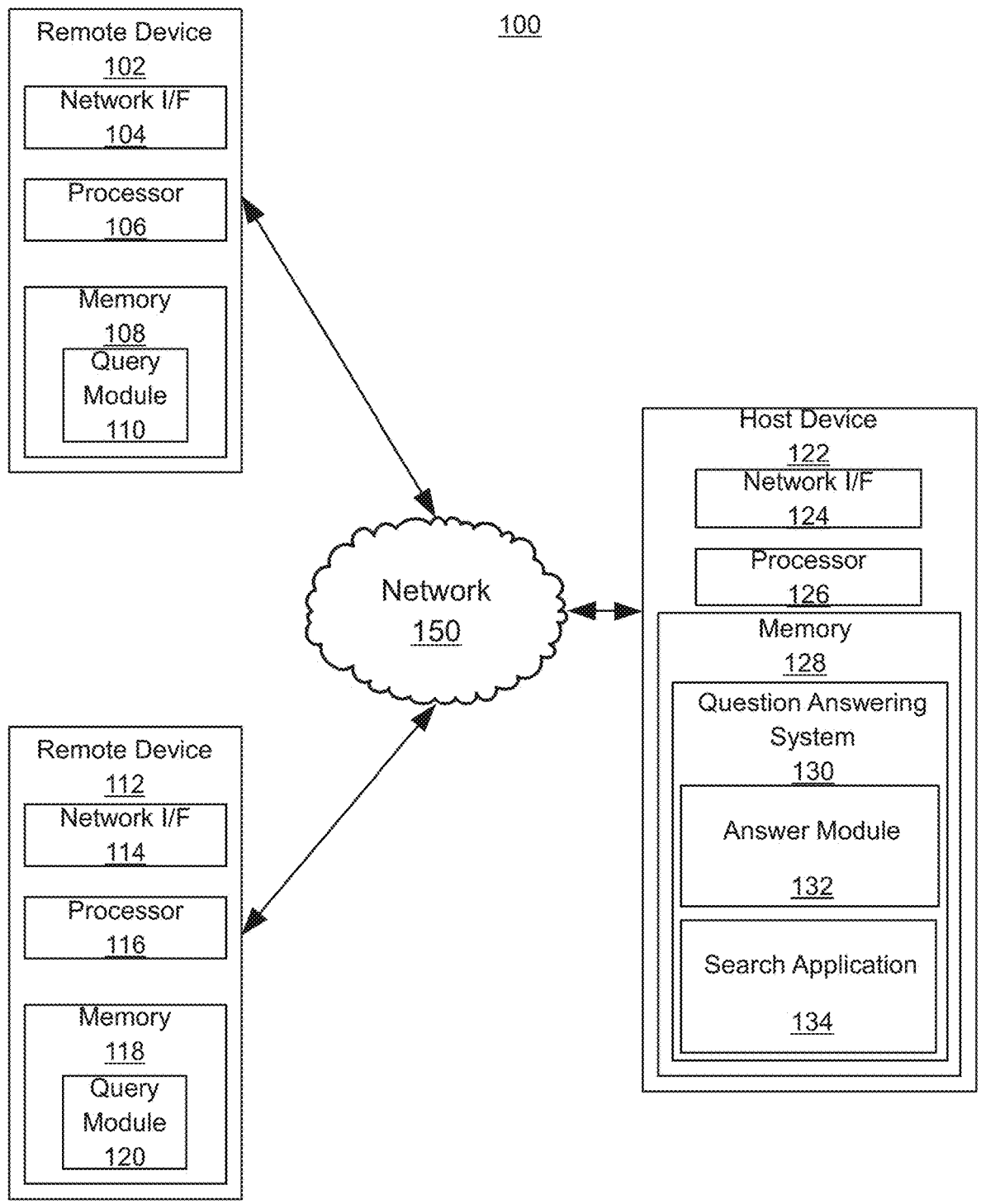
FIG. 1 is a diagrammatic illustration of an example computing environment, according to embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the disclosure relate to NER and ERD in free texts using an infinite mixture topic modeling (IMTM) technique with a neural network. The IMTM technique can construct entity chains among medical events (e.g., in an unsupervised fashion) and a neural entity pair refiner (NEPR) technique to improve performance (e.g., in a supervised fashion). In embodiments, the entity chain may include identical entity chains. Features may consider uncertainty of entity data (e.g., numbers) in each document. The dynamicity of the IMTM technique in generating new entities may have positive impacts with respect to the need of pre-estimation of entity numbers (e.g., reducing the need/demand for such pre-estimation of entity numbers). In embodiments, traceable longitudinal electronic health records facilitated by the NER and ERDs (e.g., identical NER and ERDs) may be constructed. Aspects related to a semi-supervised feature may have positive impacts with respect to a level of dependency on training data (e.g., reduce or in certain instances eliminate such dependencies). Using the IMTM technique in combination with the NEPR technique may provide various performance or efficiency benefits.

Features described herein may relate to cognitive computing in a medical or healthcare environment to facilitate dynamic clinical decision support. An entity may indicate an object or set of objects (e.g., in the real world). The textual reference to an entity may be termed a mention. A mention can include nouns, pronouns, phrases, verbal phrases, etc. which may be included in medical/clinical notes. Identical NER and ERD can include a process of clustering identical mentions, finding mentions referring to the same entities and identical mentions with respect to entity chains (e.g., coreference resolution in natural language processing). Topic modeling can include a statistical process of discovering the abstract topics that occur in a collection of documents. It may be used as a text-mining tool for discovery of hidden semantic structures in a text body. In certain embodiments, aspects may be implemented in a cloud environment (e.g., a medical cloud environment, a cognitive computing cloud environment). Aspects described herein may facilitate medical informatics research or clinical practice. To illustrate, disclosed aspects may address challenge in clinical decision support, cohort identification, or patient risk prediction and analysis.

NER and ERD systems may have various challenges. In particular, current clinical/medical identical NER and ERD systems have problems which may be addressed. Supervised models, such as pairwise classification, both strongly depend on annotated corpus which includes less portability and may include difficult to catch global information which can lead to an uninformed decision. Rule based deterministic systems, like the multi-pass sieve require well-crafted features or rule generations. Unsupervised models, like, pure Bayesian framework includes randomness which reduces the result consistency and mostly rely on co-occurrences. Disclosed aspects account for and address these challenges using a semi-supervised technique, utilizing both structured clinical notes and unstructured clinical notes, are capable of operating in a global fashion, have flexible feature extractions, use integration of a Bayesian technique, utilize neural entity pair refiner, have portability, and may produce more consistent results.

Aspects of the disclosure relate to a system, method, and computer program product for entity model establishment using an IMTM technique. A set of event data which corresponds to a set of events may be detected. Using the IMTM technique, the set of event data which corresponds to the set of events may be analyzed. Based on analyzing the set of event data using the IMTM technique, a set of entity models for the set of events may be determined. Based on the set of entity models for the set of events, a subset of the set of entity models for the set of events may be established. Altogether, aspects of the disclosure can have performance or efficiency benefits. Aspects described herein may save resources such as bandwidth, disk, processing, or memory.

In embodiments, the set of event data which corresponds to the set of events is ingested using the IMTM technique. A certain group of mention elements of the set of event data may be processed using the IMTM technique. As such, a respective mention element of the certain group of mention elements may correlate to one or more distinct entity elements. In various embodiments, the set of event data which corresponds to the set of events may be clustered using a similarity metric and based on analyzing the set of event data using the IMTM technique. In certain embodiments, a set of IMTM parameters may be derived for utilization by the IMTM technique using a Gibbs sampling technique with respect to the set of event data.

In embodiments, the set of entity models for the set of events may be analyzed using a neural entity pair refining (NEPR) technique. Based on analyzing the set of entity models using the NEPR technique, the subset of the set of entity models for the set of events can be determined. In various embodiments, a set of features may be extracted using a natural language processing technique. The set of features can both be indicated by the set of entity models and be derived from the set of event data. Using the IMTM technique in combination with the NEPR technique may provide various performance or efficiency benefits.

Turning now to the figures, FIG. 1 is a diagrammatic illustration of an exemplary computing environment, consistent with embodiments of the present disclosure. In certain embodiments, the environment 100 can include one or more remote devices 102, 112 and one or more host devices 122. Remote devices 102, 112 and host device 122 may be distant from each other and communicate over a network 150 in which the host device 122 comprises a central hub from which remote devices 102, 112 can establish a communication connection. Alternatively, the host device and remote devices may be configured in any other suitable relationship (e.g., in a peer-to-peer or other relationship).

In certain embodiments the network 100 can be implemented by any number of any suitable communications media (e.g., wide area network (WAN), local area network (LAN), Internet, Intranet, etc.). Alternatively, remote devices 102, 112 and host devices 122 may be local to each other, and communicate via any appropriate local communication medium (e.g., local area network (LAN), hardwire, wireless link, Intranet, etc.). In certain embodiments, the network 100 can be implemented within a cloud computing environment, or using one or more cloud computing services. Consistent with various embodiments, a cloud computing environment can include a network-based, distributed data processing system that provides one or more cloud computing services. In certain embodiments, a cloud computing environment can include many computers, hundreds or thousands of them, disposed within one or more data centers and configured to share resources over the network.

In certain embodiments, host device 122 can include a question answering system 130 (also referred to herein as a QA system) having a search application 134 and an answer module 132. In certain embodiments, the search application may be implemented by a conventional or other search engine, and may be distributed across multiple computer systems. The search application 134 can be configured to search one or more databases or other computer systems for content that is related to a question input by a user at a remote device 102, 112.

In certain embodiments, remote devices 102, 112 enable users to submit questions (e.g., search requests or other queries) to host devices 122 to retrieve search results. For example, the remote devices 102, 112 may include a query module 120 (e.g., in the form of a web browser or any other suitable software module) and present a graphical user (e.g., GUI, etc.) or other interface (e.g., command line prompts, menu screens, etc.) to solicit queries from users for submission to one or more host devices 122 and further to display answers/results obtained from the host devices 122 in relation to such queries.

Consistent with various embodiments, host device 122 and remote devices 102, 112 may be computer systems preferably equipped with a display or monitor. In certain embodiments, the computer systems may include at least one processor 106, 116, 126 memories 108, 118, 128 and/or internal or external network interface or communications devices 104, 114, 124 (e.g., modem, network cards, etc.), optional input devices (e.g., a keyboard, mouse, or other input device), and any commercially available and custom software (e.g., browser software, communications software, server software, natural language processing software, search engine and/or web crawling software, filter modules for filtering content based upon predefined criteria, etc.). In certain embodiments, the computer systems may include server, desktop, laptop, and hand-held devices. In addition, the answer module 132 may include one or more modules or units to perform the various functions of present disclosure embodiments described below (e.g., receiving an input question, evaluating the quality of the input question, assigning a set of quality values, and generating an icon), and may be implemented by any combination of any quantity of software and/or hardware modules or units.

Figure 2:
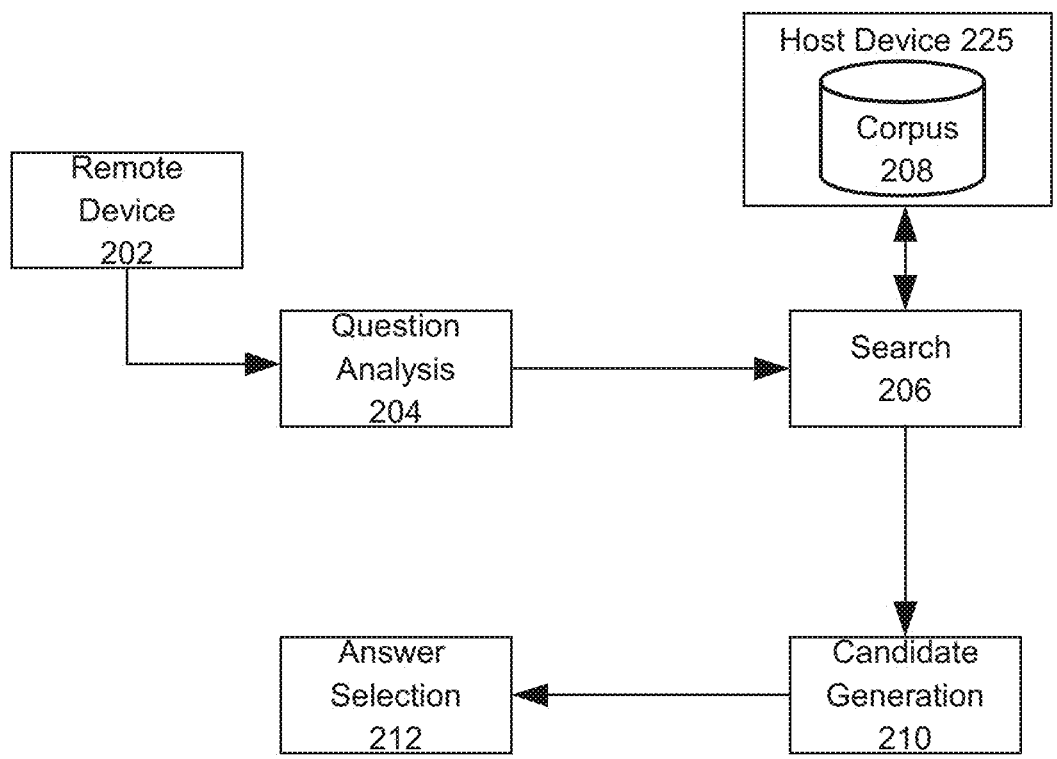
FIG. 2 is a system diagram depicting a high level logical architecture for a question answering system, according to embodiments.

FIG. 2 is a system diagram depicting a high-level logical architecture 200 for a question answering system (also referred to herein as a QA system), consistent with embodiments of the present disclosure. Aspects of FIG. 2 are directed toward components for use with a QA system. In certain embodiments, the question analysis component 204 can receive a natural language question from a remote device 202, and can analyze the question to produce, minimally, the semantic type of the expected answer. The search component 206 can formulate queries from the output of the question analysis component 204 and may consult various resources such as the internet or one or more knowledge resources, e.g., databases, corpora 208, to retrieve documents, passages, web-pages, database tuples, etc., that are relevant to answering the question. For example, as shown in FIG. 2, in certain embodiments, the search component 206 can consult a corpus of information 208 on a host device 225. The candidate answer generation component 210 can then extract from the search results potential (candidate) answers to the question, which can then be scored and ranked by the answer selection component 212 which may produce a final ranked list of answers with associated confidence measure values.

The various components of the exemplary high level logical architecture for a QA system described above may be used to implement various aspects of the present disclosure. For example, the question analysis component 204 could, in certain embodiments, be used to process a natural language question for which relevant images can be provided. Further, the search component 206 can, in certain embodiments, be used to perform a search of a corpus of information 208 for a set of images that are related to an answer to an input question to the QA system. The candidate generation component 210 can be used to identify a set of candidate images based on the results of the search component 206. Further, the answer selection component 212 can, in certain embodiments, be used to determine and select a subset of the set of candidate images to provide in a display area. In certain embodiments, the determination of the subset of the candidate images can be based on a confidence value of the set of images and a designated display specification.

Figure 3:
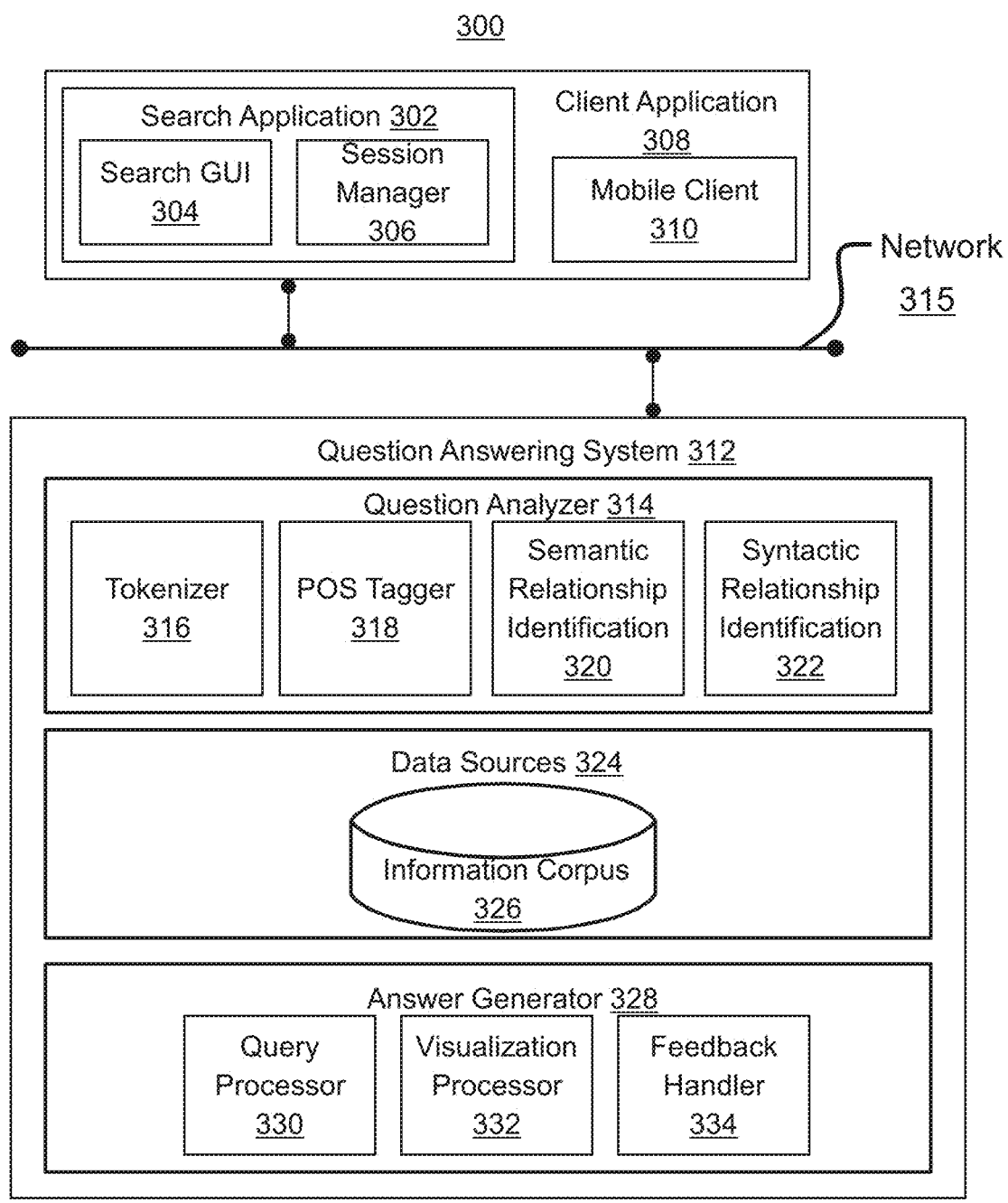
FIG. 3 is a block diagram illustrating a question answering system to generate answers to one or more input questions, according to embodiments.

FIG. 3 is a block diagram illustrating a question answering system (also referred to herein as a QA system) to generate answers to one or more input questions, consistent with various embodiments of the present disclosure. Aspects of FIG. 3 are directed toward an exemplary system architecture 300 of a question answering system 312 to generate answers to queries (e.g., input questions). In certain embodiments, one or more users may send requests for information to QA system 312 using a remote device (such as remote devices 102, 112 of FIG. 1). QA system 312 can perform methods and techniques for responding to the requests sent by one or more client applications 308. Client applications 308 may involve one or more entities operable to generate events dispatched to QA system 312 via network 315. In certain embodiments, the events received at QA system 312 may correspond to input questions received from users, where the input questions may be expressed in a free form and in natural language.

A question (similarly referred to herein as a query) may be one or more words that form a search term or request for data, information or knowledge. A question may be expressed in the form of one or more keywords. Questions may include various selection criteria and search terms. A question may be composed of complex linguistic features, not only keywords. However, keyword-based search for answer is also possible. In certain embodiments, using unrestricted syntax for questions posed by users is enabled. The use of restricted syntax results in a variety of alternative expressions for users to better state their needs.

Consistent with various embodiments, client applications 308 can include one or more components such as a search application 302 and a mobile client 310. Client applications 308 can operate on a variety of devices. Such devices include, but are not limited to, mobile and handheld devices, such as laptops, mobile phones, personal or enterprise digital assistants, and the like; personal computers, servers, or other computer systems that access the services and functionality provided by QA system 312. For example, mobile client 310 may be an application installed on a mobile or other handheld device. In certain embodiments, mobile client 310 may dispatch query requests to QA system 312.

Consistent with various embodiments, search application 302 can dispatch requests for information to QA system 312.

In certain embodiments, search application 302 can be a client application to QA system 312. In certain embodiments, search application 302 can send requests for answers to QA system 312. Search application 302 may be installed on a personal computer, a server or other computer system. In certain embodiments, search application 302 can include a search graphical user interface (GUI) 304 and session manager 306. Users may enter questions in search GUI 304. In certain embodiments, search GUI 304 may be a search box or other GUI component, the content of which represents a question to be submitted to QA system 312. Users may authenticate to QA system 312 via session manager 306. In certain embodiments, session manager 306 keeps track of user activity across sessions of interaction with the QA system 312. Session manager 306 may keep track of what questions are submitted within the lifecycle of a session of a user. For example, session manager 306 may retain a succession of questions posed by a user during a session. In certain embodiments, answers produced by QA system 312 in response to questions posed throughout the course of a user session may also be retained. Information for sessions managed by session manager 306 may be shared between computer systems and devices.

In certain embodiments, client applications 308 and QA system 312 can be communicatively coupled through network 315, e.g. the Internet, intranet, or other public or private computer network. In certain embodiments, QA system 312 and client applications 308 may communicate by using Hypertext Transfer Protocol (HTTP) or Representational State Transfer (REST) calls. In certain embodiments, QA system 312 may reside on a server node. Client applications 308 may establish server-client communication with QA system 312 or vice versa. In certain embodiments, the network 315 can be implemented within a cloud computing environment, or using one or more cloud computing services. Consistent with various embodiments, a cloud computing environment can include a network-based, distributed data processing system that provides one or more cloud computing services.

Consistent with various embodiments, QA system 312 may respond to the requests for information sent by client applications 308, e.g., posed questions by users. QA system 312 can generate answers to the received questions. In certain embodiments, QA system 312 may include a question analyzer 314, data sources 324, and answer generator 328. Question analyzer 314 can be a computer module that analyzes the received questions. In certain embodiments, question analyzer 314 can perform various methods and techniques for analyzing the questions syntactically and semantically. In certain embodiments, question analyzer 314 can parse received questions. Question analyzer 314 may include various modules to perform analyses of received questions. For example, computer modules that question analyzer 314 may include, but are not limited to a tokenizer 316, part-of-speech (POS) tagger 318, semantic relationship identification 320, and syntactic relationship identification 322.

Consistent with various embodiments, tokenizer 316 may be a computer module that performs lexical analysis. Tokenizer 316 can convert a sequence of characters into a sequence of tokens. Tokens may be string of characters typed by a user and categorized as a meaningful symbol. Further, in certain embodiments, tokenizer 316 can identify word boundaries in an input question and break the question or any text into its component parts such as words, multi-word tokens, numbers, and punctuation marks. In certain embodiments, tokenizer 316 can receive a string of characters, identify the lexemes in the string, and categorize them into tokens.

Consistent with various embodiments, POS (part of speech) tagger 318 can be a computer module that marks up a word in a text to correspond to a particular part of speech. POS tagger 318 can read a question or other text in natural language and assign a part of speech to each word or other token. POS tagger 318 can determine the part of speech to which a word corresponds based on the definition of the word and the context of the word. The context of a word may be based on its relationship with adjacent and related words in a phrase, sentence, question, or paragraph. In certain embodiments, context of a word may be dependent on one or more previously posed questions. Examples of parts of speech that may be assigned to words include, but are not limited to, nouns, verbs, adjectives, adverbs, and the like. Examples of other part of speech categories that POS tagger 318 may assign include, but are not limited to, comparative or superlative adverbs, wh-adverbs, conjunctions, determiners, negative particles, possessive markers, prepositions, wh-pronouns, and the like. In certain embodiments, POS tagger 316 can tag or otherwise annotates tokens of a question with part of speech categories. In certain embodiments, POS tagger 316 can tag tokens or words of a question to be parsed by QA system 312.

Consistent with various embodiments, semantic relationship identification 320 may be a computer module that can identify semantic relationships of recognized entities in questions posed by users. In certain embodiments, semantic relationship identification 320 may determine functional dependencies between entities, the dimension associated to a member, and other semantic relationships.

Consistent with various embodiments, syntactic relationship identification 322 may be a computer module that can identify syntactic relationships in a question composed of tokens posed by users to QA system 312. Syntactic relationship identification 322 can determine the grammatical structure of sentences, for example, which groups of words are associated as "phrases" and which word is the subject or object of a verb. In certain embodiments, syntactic relationship identification 322 can conform to a formal grammar.

In certain embodiments, question analyzer 314 may be a computer module that can parse a received query and generate a corresponding data structure of the query. For example, in response to receiving a question at QA system 312, question analyzer 314 can output the parsed question as a data structure. In certain embodiments, the parsed question may be represented in the form of a parse tree or other graph structure. To generate the parsed question, question analyzer 130 may trigger computer modules 132-144. Question analyzer 130 can use functionality provided by computer modules 316-322 individually or in combination. Additionally, in certain embodiments, question analyzer 130 may use external computer systems for dedicated tasks that are part of the question parsing process.

Consistent with various embodiments, the output of question analyzer 314 can be used by QA system 312 to perform a search of one or more data sources 324 to retrieve information to answer a question posed by a user. In certain embodiments, data sources 324 may include data warehouses, information corpora, data models, and document repositories. In certain embodiments, the data source 324 can be an information corpus 326. The information corpus 326 can enable data storage and retrieval. In certain embodiments, the information corpus 326 may be a storage mechanism that houses a standardized, consistent, clean and integrated form of data. The data may be sourced from various operational systems. Data stored in the information corpus 326 may be structured in a way to specifically address reporting and analytic requirements. In one embodiment, the information corpus may be a relational database (e.g., conform to an ontology). In some example embodiments, data sources 324 may include one or more document repositories.

In certain embodiments, answer generator 328 may be a computer module that generates answers to posed questions. Examples of answers generated by answer generator 328 may include, but are not limited to, answers in the form of natural language sentences; reports, charts, or other analytic representation; raw data; web pages, and the like.

Consistent with various embodiments, answer generator 328 may include query processor 330, visualization processor 332 and feedback handler 334. When information in a data source 324 matching a parsed question is located, a technical query associated with the pattern can be executed by query processor 330. Based on retrieved data by a technical query executed by query processor 330, visualization processor 332 can render visualization of the retrieved data, where the visualization represents the answer. In certain embodiments, visualization processor 332 may render various analytics to represent the answer including, but not limited to, images, charts, tables, dashboards, maps, and the like. In certain embodiments, visualization processor 332 can present the answer to the user in understandable form.

In certain embodiments, feedback handler 334 can be a computer module that processes feedback from users on answers generated by answer generator 328. In certain embodiments, users may be engaged in dialog with the QA system 312 to evaluate the relevance of received answers. Answer generator 328 may produce a list of answers corresponding to a question submitted by a user. The user may rank each answer according to its relevance to the question. In certain embodiments, the feedback of users on generated answers may be used for future question answering sessions.

The various components of the exemplary question answering system described above may be used to implement various aspects of the present disclosure. For example, the client application 308 could be used to receive an input question having a set of query attributes. The question analyzer 314 could, in certain embodiments, be used to evaluate the quality of the input question by comparing the set of query attributes to a set of assessment criteria. Further, the question answering system 312 could, in certain embodiments, be used to perform a search of an information corpus 326 for data that may provide an answer to the input question. The answer generator 328 can be used assign a set of quality values to the set of query attributes, as well as use the assigned set of quality values and the set of query attributes to generate an icon that indicates a visual representation of the quality of the input question. Further, the visualization processor 332 can, in certain embodiments, be used to render the icon (e.g., a digital face icon) in a designated display area.

Figure 4:
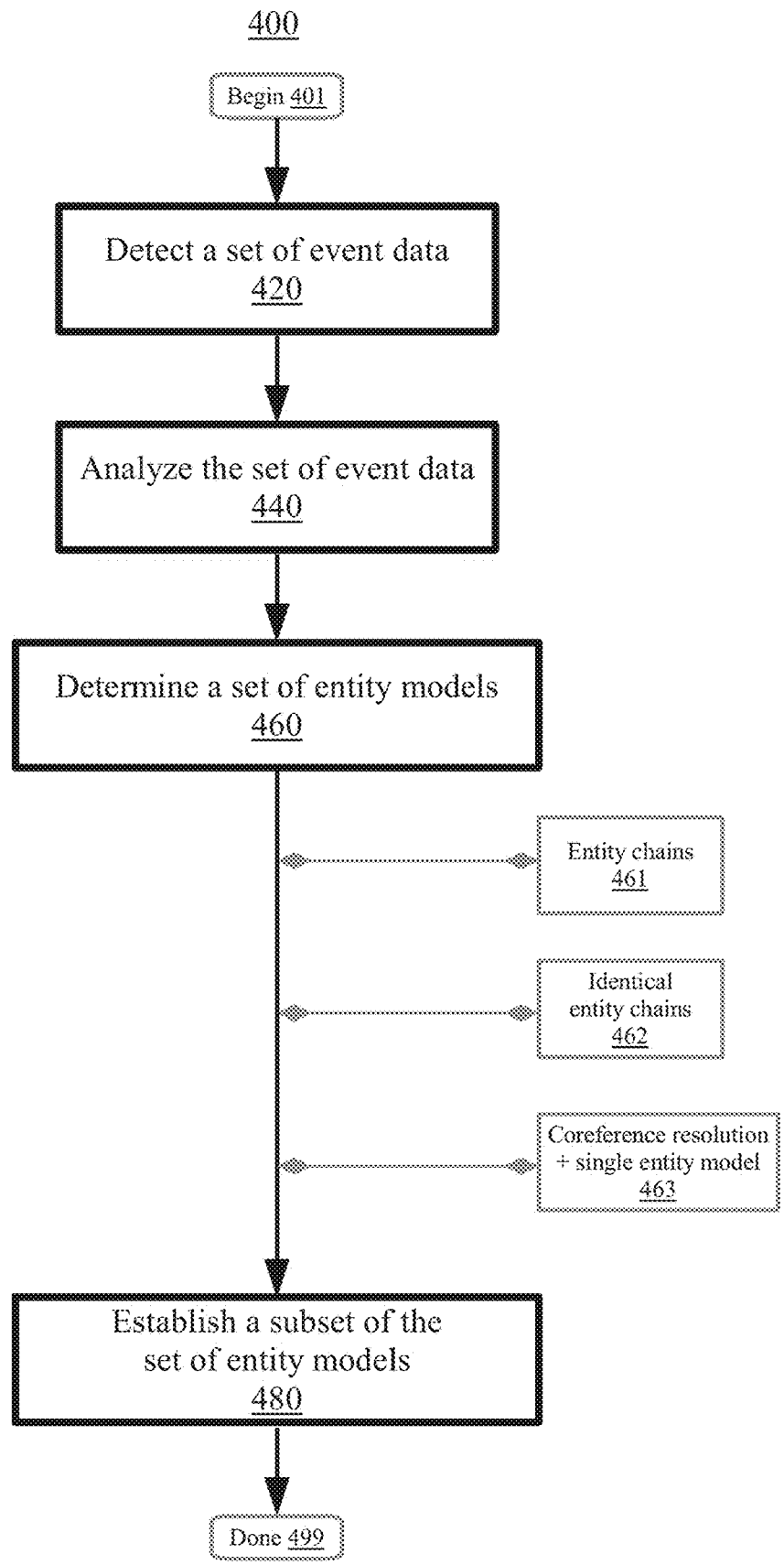
FIG. 4 is a flowchart illustrating a method for entity model establishment using an infinite mixture topic modeling (IMTM) technique, according to embodiments.

FIG. 4 is a flowchart illustrating a method 400 for entity model establishment using an IMTM technique. Aspect may be semi-supervised and highly portable. Features may have dependence on manual annotations of coreferring relations below a threshold dependence (e.g., limited dependencies). Similarly, knowledge below a threshold may be necessary (e.g., limited knowledge needed). Elements may integrate into a cloud computing environment. Coreference chains constructed among clinical notes may facilitate the construction of a robust clinical decision support system. Accordingly, positive impacts on cohort identification, patient risk analysis, and various forecasts or predictions may result. The method 400 may begin at block 401.

At block 420, a set of event data may be detected. The set of event data may correspond to a set of events. Generally, detecting can include sensing, discovering, recognizing, resolving, or otherwise identifying the set of event data. The set of events can include states, conditions, modes of being, circumstances, or the like. For example, in the medical context, the set of events can include sick, ill, pregnant, vomiting, nausea, gastrointestinal symptoms, cancer in remission, broken bone, tumor growth, or the like. The set of event data may include identifiers which represent the events. For example, the word pregnant may indicate someone who is pregnant. Similarly, the word 'expecting' may also indicate that the person is pregnant. Data such as 102 degree temperature, may indicate an individual has the flu. Accordingly, the set of event data may be in a structured or unstructured format. As such, the set of event data may be detected in clinical notes which may be found in natural language computer text, handwritten text, a relational database, or various other formats consistent therewith.

At block 440, the set of event data which corresponds to the set of events may be analyzed. The analyzing may be performed using the IMTM technique. For instance, analyzing can include extracting (e.g., creating a derivation), examining (e.g., performing an inspection), scanning (e.g., reviewing a sample), evaluating (e.g., generating an appraisal), dissecting (e.g., scrutinizing an attribute), resolving (e.g., ascertaining an observation/conclusion/answer), parsing (e.g., deciphering a construct), querying (e.g., asking a question), searching (e.g., exploring for a reason/ground/motivation), comparing (e.g., relating an assessment), classifying (e.g., assigning a designation), or categorizing (e.g., organizing by a feature). Data analysis may include a process of inspecting, cleaning, transforming, or modeling data to discover useful information, suggest conclusions, or support decisions. Data analysis can extract information/patterns from a data set and transform/translate it into an understandable structure (e.g., a data report which can be provided/furnished) for further use. For example, the IMTM technique may resolve one or more coreferent relations between a plurality of mentions. To illustrate, a similarity measurement between two mentions may evaluate the likelihood that two mentions are coreferent. The similarity score may be used to determine if there is an antecedent of the given mention.

At block 460, a set of entity models for the set of events may be determined. The determining may be performed based on analyzing the set of event data using the IMTM technique. Generally, determining can include formulating, resolving, computing, calculating, identifying, or otherwise ascertaining the set of entity models. For example, with respect to the text: "The patient presents with gastrointestinal symptoms including nausea, vomiting. She has had symptoms for 10 days. In fact, is having that problem since early pregnancy but worst since 10 days.", various mentions may be extracted such as: "The patient, gastrointestinal symptoms, nausea, vomiting, She, symptoms, that problem, early pregnancy". Accordingly, one or more entities may be derived such as "The patient, gastrointestinal symptoms, nausea, vomiting, early pregnancy". Accordingly, five entities may be deemed to have been discovered among the short text forming five entity models. Other possibilities consistent with aspects described herein are considered.

In embodiments, the set of entity models may be configured to include a set of entity chains at block 461. The subset of the set of entity models may be configured to include a subset of the set of entity chains. In clinical notes, there may be a significant number of singular mentions with a long chain of patient mentions. Mentions may be chained based on similarity using machine learning techniques such as natural language processing. Various related items may be mapped or linked together in an entity chain. The mentions may be linked such when having a similar/same meaning in context (e.g., "she is expecting" and "she is pregnant", "feeling just a little under the weather" and "ill but it doesn't seem serious"). In embodiments, the set of entity models may be configured to include a set of identical entity chains at block 462. The subset of the set of entity models may be configured to include a subset of the set of identical entity chains. The identical entity chains may have the same meaning (e.g., "running a temperature of 3 degrees above normal" and "running a temperature of 101.6 degrees") or be identical in verbiage (e.g., "nausea" and "Nausea"), or the like. Diverse entity chains are also possible. In embodiments, the set of entity models may be configured to indicate at least one coreference resolution at block 463. Coreference resolution can include expressions that refer to the same item/entity in a text. Other possibilities consistent with aspects described herein are considered.

At block 480, a subset of the set of entity models for the set of events may be established. Generally, establishing can include creating, instantiating, formulating, constructing, building, assembling, structuring, producing, or otherwise generating. The establishing may be performed based on the set of entity models for the set of events. In embodiments, all of the entity models for the set of events may be established. In certain embodiments, less than all of the entity models for the set of events may be established. In various embodiments, the subset of the set of entity models may be configured to include a single entity model (e.g., one chain is produced). Accordingly, a selection may occur based on a weighted value of what may be considered to be the 'best' chains. Other possibilities consistent with aspects described herein are considered.

Method 400 concludes at block 499. Aspects of method 400 may provide performance or efficiency benefits related to entity model establishment. Aspects may include a relatively more generic framework with respect to diverse relation detection tasks. Elements may include resolution of temporal relations and construction of time-series chains for longitudinal data. Named entity detection and relation discovery among them may be facilitated. A semantic network may be improved. A relatively more accurate knowledge graph can be built. Features can be adapted to drug-drug-interaction studies in medical informatics. Drug-disease relation discovery can be made, in embodiments. A gene pattern discovery framework can be established and assembled. Aspects may save resources such as bandwidth, disk, processing, or memory.

Figure 5:
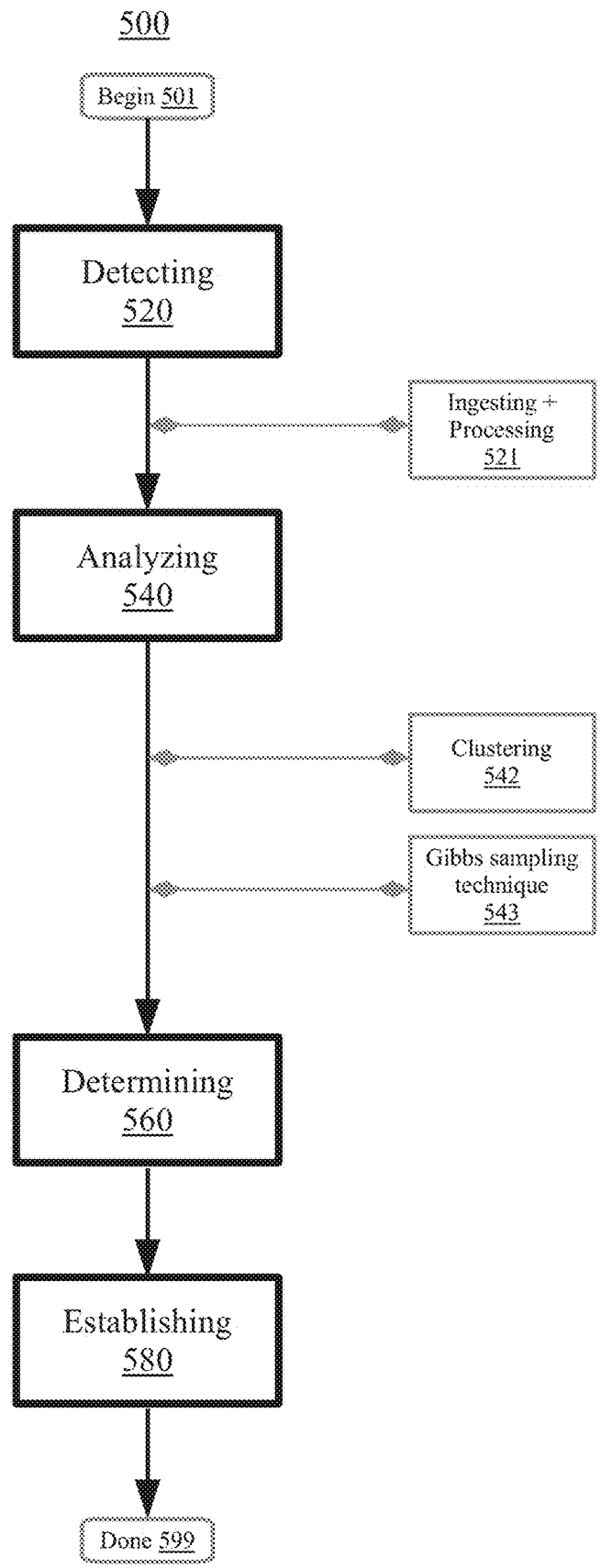
FIG. 5 is a flowchart illustrating a method for entity model establishment using an IMTM technique, according to embodiments.

FIG. 5 is a flowchart illustrating a method 500 for entity model establishment using an IMTM technique. Aspects of the method 500 may be similar or the same as aspects of method 400/600/700, and aspects may be utilized interchangeably. The method 500 may begin at block 501. At block 520, a set of event data may be detected. The set of event data may correspond to a set of events.

In embodiments, the set of event data which corresponds to the set of events may be ingested at block 521. Generally, ingesting can include detecting, analyzing, sensing, receiving, collecting, gathering, transforming, importing, or otherwise capturing the set of event data which corresponds to the set of events. The ingesting may be performed using the IMTM technique. A certain group of mention elements of the set of event data may be processed. The processing may be performed using the IMTM technique. A respective mention element of the certain group of mention elements may correlate to one or more distinct entity elements. Accordingly, the IMTM technique handles an uncertain number of entities given a certain number of mentions (e.g., given a document, processing the document without a count of how many coreferring mentions exist). The IMTM technique, helped with Gibbs sampling, can generate entities close to the actual ones (e.g., of the real clinical notes) within a threshold tolerance (e.g., a percentage such as 10% or 5%) or the like. Other possibilities consistent with aspects described herein are considered.

At block 540, the set of event data which corresponds to the set of events may be analyzed. The analyzing may be performed using the IMTM technique. In embodiments, the set of event data which corresponds to the set of events may be clustered at block 542. Generally, clustering can include grouping, aligning, combining, arranging, configuring, or otherwise ordering. The clustering may be performed using a similarity metric (e.g., how alike, a homogeneous score, based on attributes of the data such as syntax, semantics, etc.) and based on analyzing the set of event data using the IMTM technique. Various clustering techniques may be used. Clustering techniques may include a method or algorithm for performing statistical data analysis with respect to the set of event data. As examples, the clustering technique may include connectivity models (e.g., hierarchical clustering), centroid models (e.g., k-means clustering), distribution models (e.g., multivariate normal distributions), density models (e.g., density-based spatial clustering, ordered point identification), subspace models (e.g., co-clustering, biclustering), and the like. Other possibilities consistent with aspects described herein are considered.

In embodiments, a set of IMTM parameters may be derived at block 543. Generally, deriving can include formulating, extracting, computing, generating, or otherwise identifying. The deriving may be performed for utilization by the IMTM technique. The deriving may be performed using a Gibbs sampling technique with respect to the set of event data. Gibbs sampling is a Markov-chain Monte Carlo simulation that may yield a straightforward algorithm for approximate inference (e.g., in high-dimensional models). Accordingly, parameters and parameter values may be ascertained (e.g., related to the entities and mentions). A parameter can include an attribute, characteristic, or setting that may be used to define one or more models such as a set of entity models. Other possibilities consistent with aspects described herein are considered.

At block 560, a set of entity models for the set of events may be determined. The determining may be performed based on analyzing the set of event data using the IMTM technique. At block 580, a subset of the set of entity models for the set of events may be established. The establishing may be performed based on the set of entity models for the set of events. Method 500 concludes at block 599. Aspects of method 500 may provide performance or efficiency benefits related to entity model establishment. Aspects may save resources such as bandwidth, disk, processing, or memory.

Figure 6:
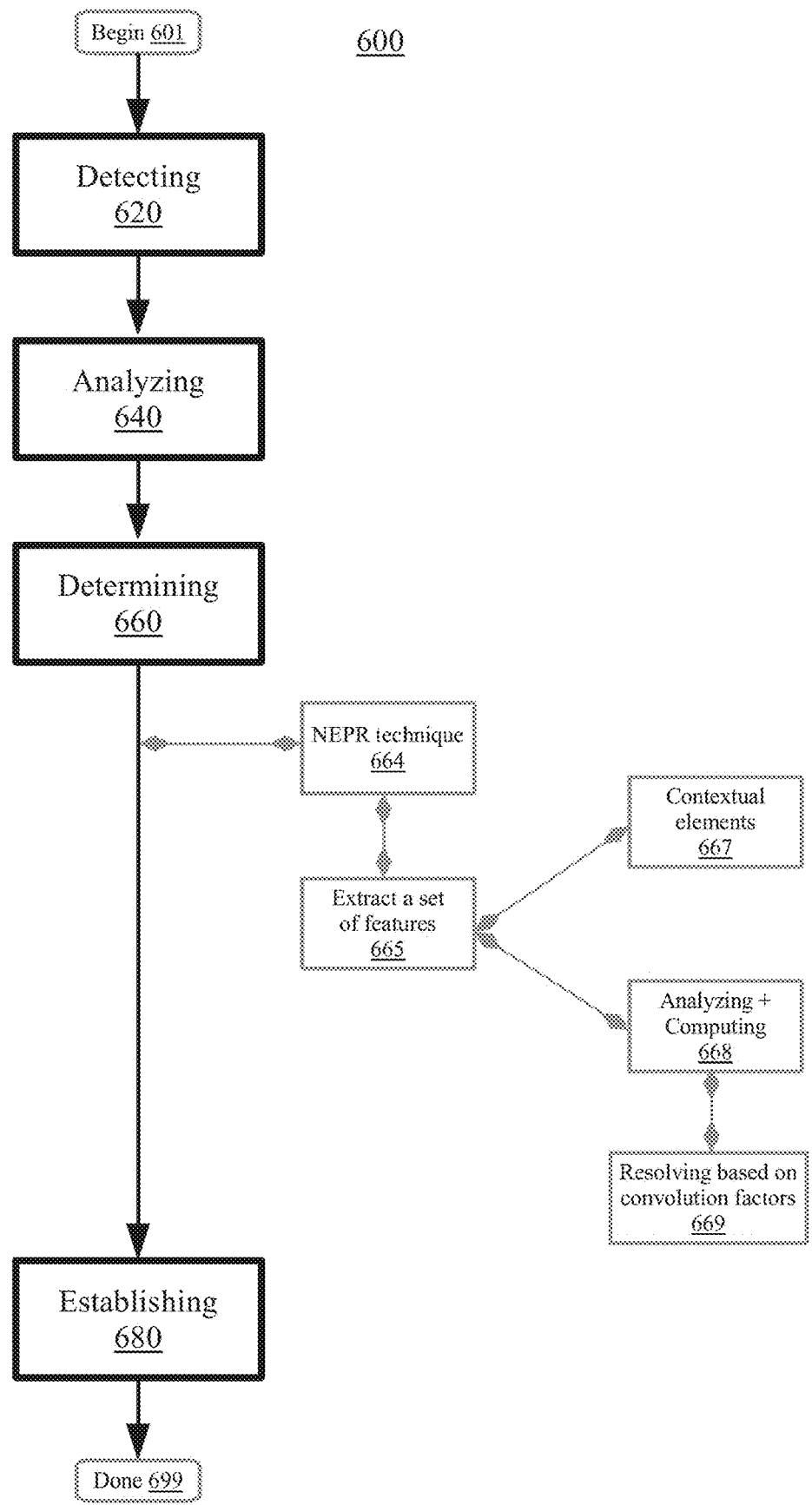
FIG. 6 is a flowchart illustrating a method for entity model establishment using an IMTM technique, according to embodiments.

FIG. 6 is a flowchart illustrating a method 600 for entity model establishment using an IMTM technique. Aspects of the method 600 may be similar or the same as aspects of method 400/500/700, and aspects may be utilized interchangeably. The method 600 may begin at block 601. At block 620, a set of event data may be detected. The set of event data may correspond to a set of events. At block 640, the set of event data which corresponds to the set of events may be analyzed. The analyzing may be performed using the IMTM technique. At block 660, a set of entity models for the set of events may be determined. The determining may be performed based on analyzing the set of event data using the IMTM technique.

In embodiments, the set of entity models for the set of events may be analyzed at block 664. The analyzing may be performed using a neural entity pair refining (NEPR) technique. The NEPR technique may be utilized to refine entity pairs generated by the IMTM technique. The subset of the set of entity models for the set of events may be determined. The determining may be performed based on analyzing the set of entity models using the NEPR technique. The NEPR technique may include feature extraction (e.g., using natural language processing for extraction of information from electronic medical record clinical free-text). As such, a set of features may be extracted at block 665. The set of features may be both indicated by the set of entity models and derived from the set of event data. The extracting may be performed using a natural language processing technique. Various combinations of the features may be considered. The combinations may be refined or pooled for the NEPR technique to achieve a threshold level of accuracy, precision, or the like. Other possibilities consistent with aspects described herein are considered.

In embodiments, the set of features may be configured to include a set of contextual elements at block 667. Contextual elements can include semantic or syntactic features/components. Punctuation of surrounding phrases may indicate meaning of various a certain word. A single active voice sentence in a paragraph of passive voice sentence may be indicative of a relative level of importance. Emojis and the placement thereof can indicate one or more components of the set of event data. In general, each feature may be analyzed based on the context of the respective feature. Other possibilities consistent with aspects described herein are considered.

In embodiments, a set of combinations of the set of features may be analyzed at block 668. A set of convolution factors may be computed. Generally, computing can include formulating, calculating, ascertaining, measuring, estimating, or otherwise determining the set of convolution factors. The computing may be performed with respect to the set of combinations of the set of features. In general, convolution is a mathematical operation on two functions that produces a third function. The third function may be presented as a modified version of one of the original functions, giving the integral of the pointwise multiplication of the two functions as a function of the amount that one of the original functions is translated. As such, convolution factors may be attributes, characteristics, or parameters which influence the nature of such a third function. Convolution may be different from cross-correlation or autocorrelation. Other possibilities consistent with aspects described herein are considered.

In embodiments, the subset of the set of entity models for the set of events may be resolved at block 669. Generally, resolving can include developing, formulating, ascertaining, computing, calculating, identifying, selecting, or otherwise determining. The resolving may be performed based on the set of convolution factors. For instance, various candidate entity models may be filtered to resolve/select only a portion of the set of entity models (e.g., a single entity model). Such filtering/narrowing may occur based on the set of convolution factors. Other possibilities consistent with aspects described herein are considered.

At block 680, a subset of the set of entity models for the set of events may be established. The establishing may be performed based on the set of entity models for the set of events. Method 600 concludes at block 699. Aspects of method 600 may provide performance or efficiency benefits related to entity model establishment. Aspects may save resources such as bandwidth, disk, processing, or memory.

Figure 7:
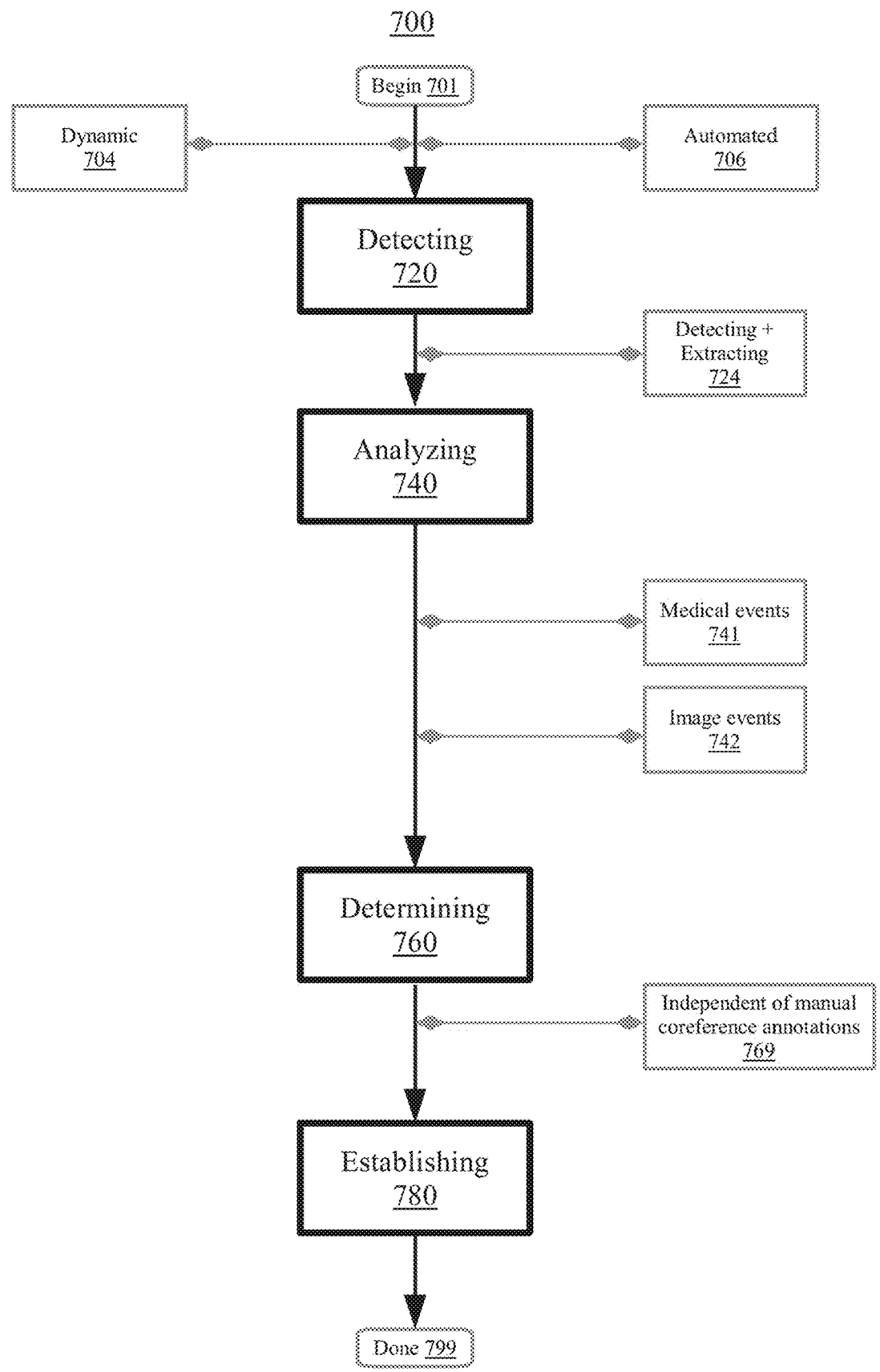
FIG. 7 is a flowchart illustrating a method for entity model establishment using an IMTM technique, according to embodiments.

FIG. 7 is a flowchart illustrating a method 700 for entity model establishment using an IMTM technique. Aspects of the method 700 may be similar or the same as aspects of method 400/500/600, and aspects may be utilized interchangeably. The method 700 may begin at block 701.

In embodiments, the detecting, the analyzing, the determining, the establishing, and the other steps described herein may each be executed in a dynamic fashion at block 704. The steps described herein may be executed in a dynamic fashion to streamline entity model establishment. For instance, the detecting, the analyzing, the determining, the establishing, and the other steps described herein may occur in real-time, ongoing, or on-the-fly. As an example, one or more steps described herein may be performed on-the-fly (e.g., running the IMTM technique and the NEPR technique in real-time) in order to streamline (e.g., facilitate, promote, enhance) entity model establishment. Other methods of performing the steps described herein in a dynamic fashion are also possible and considered.

In embodiments, the detecting, the analyzing, the determining, the establishing, and the other steps described herein may each be executed in an automated fashion at block 706. The steps described herein may be executed in an automated fashion without user intervention. In embodiments, the detecting, the analyzing, the determining, the establishing, and the other steps described herein may be carried-out by an internal entity model establishment module maintained in a persistent storage device of a local computing device (e.g., network node, multi-node server). In embodiments, the detecting, the analyzing, the determining, the establishing, and the other steps described herein may be carried-out by an external entity model establishment module hosted by a remote computing device or server (e.g., server accessible via a subscription, usage-based, or other service model). In this way, aspects of entity model establishment may be performed using automated computing machinery without manual action. Accordingly, the steps described herein may be executed in an automated fashion without user intervention or manual action (e.g., using automated computer machinery, fully machine-driven without manual stimuli). Other methods of performing the steps described herein in an automated fashion are also possible and considered.

At block 720, a set of event data may be detected. The set of event data may correspond to a set of events. In embodiments, it may be detected that the set of event data includes both structured data and unstructured data at block 724. Structured data can include information with a substantial degree of organization in a manner such that inclusion in a relational database is seamless and readily able to be searched by a straightforward query, search engine algorithms, or other search operation. Accordingly, structured data can include information (e.g., text files) displayed in titled columns and rows which can easily be ordered and processed by data mining tools (e.g., the data stored in fields in a database). Unstructured data can include information which is without an (easily) identifiable/recognizable internal structure. Accordingly, unstructured data may refer to information that does not reside in a traditional row-column database (e.g., books, journals, documents, metadata, health records, audio, video, analog data, images, files, and unstructured text such as the body of an e-mail message, Web page, or word-processor document). As such, unstructured data may include information that does not have a pre-defined data model or is not organized in a pre-defined manner. A set of features for utilization as a set of analysis parameters (e.g., constraints for the IMTM/NEPR techniques) may be extracted. The extracting may be performed using a natural language processing technique with respect to the set of event data. The natural language processing technique can include one or more computer-based algorithms configured to derive meaning from natural language content. As examples, the natural language processing technique can include algorithms configured for part-of-speech tagging, parsing, relationship extraction, sentiment analysis, information retrieval, information extraction, morphological segmentation, or the like. Other possibilities consistent with aspects described herein are considered.

At block 740, the set of event data which corresponds to the set of events may be analyzed. The analyzing may be performed using the IMTM technique. In embodiments, the set of events may be configured to include a set of medical events at block 741. A set of electronic health record data may be constructed. The set of electronic health record data may be constructed based on the subset of the set of entity models for the set of medical events. In embodiments, the set of events may be configured to include a set of image events at block 742. A set of image data may be processed. The processing may be performed based on the subset of the set of entity models for the set of image events.

At block 760, a set of entity models for the set of events may be determined. The determining may be performed based on analyzing the set of event data using the IMTM technique. In various embodiments, the set of entity models for the set of events may be determined at block 769. The determining may be performed independent of manual coreference annotation (e.g., without such annotation). The subset of the set of entity models for the set of events may be established. The establishing may be performed in response to determining the set of entity models for the set of events independent of manual coreference annotation.

At block 780, a subset of the set of entity models for the set of events may be established. The establishing may be performed based on the set of entity models for the set of events. Method 700 concludes at block 799. Aspects of method 700 may provide performance or efficiency benefits related to entity model establishment. Aspects may save resources such as bandwidth, disk, processing, or memory.

Figure 8:
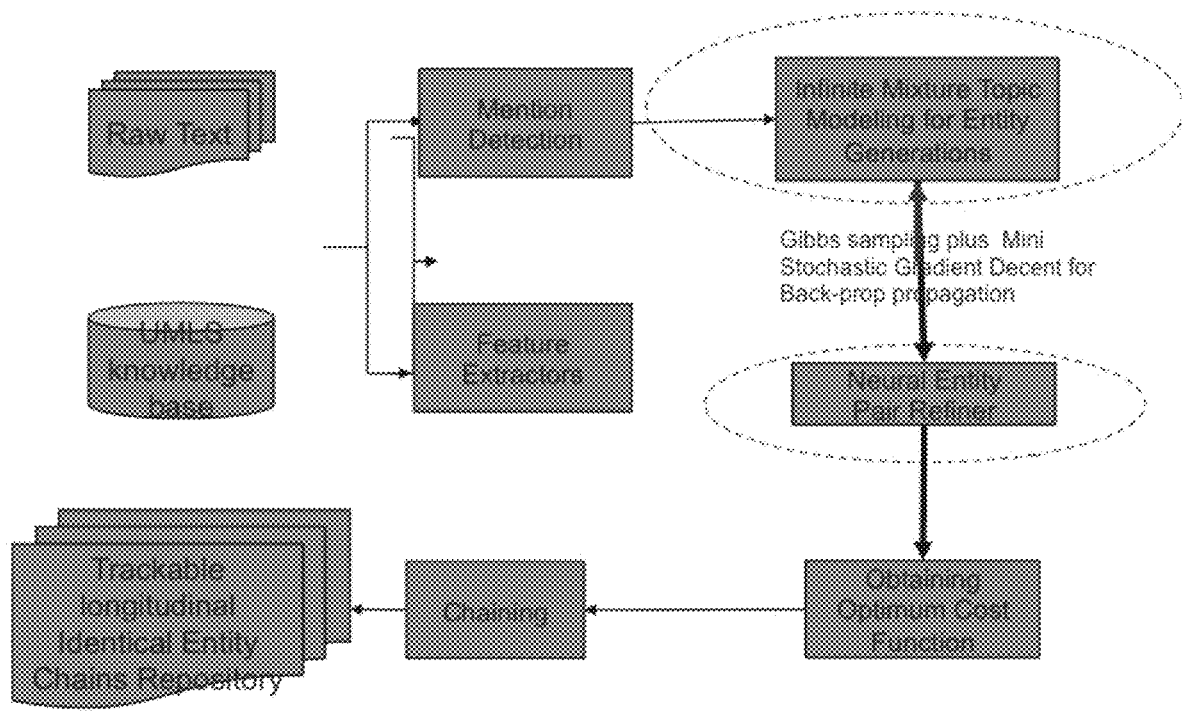
FIG. 8 illustrates an example for entity model establishment using an IMTM technique, according to embodiments.

FIG. 8 illustrates an example 800 for entity model establishment using an IMTM technique, according to embodiments. The example 800 illustrates an example system pipeline. Raw clinical notes and knowledge resources may be processed in a streamlined fashion using the example system pipeline or the like. Mentions can be retrieved and recognized from both structured and unstructured notes. Features may be extracted with language processing systems and can be utilized as constraints. Gibbs sampling may be used for parameter estimation and inferences in the loop of NER and ERDs with IMTM. A convolutional neural network can be constructed to refine each entity pair generated by the IMTM to improve the performance of the system. Identical mentions may be clustered into one chain and output into the final entity chain repository. Various other possibilities consistent with aspects described herein both explicitly and implicitly are considered.

Figure 9:
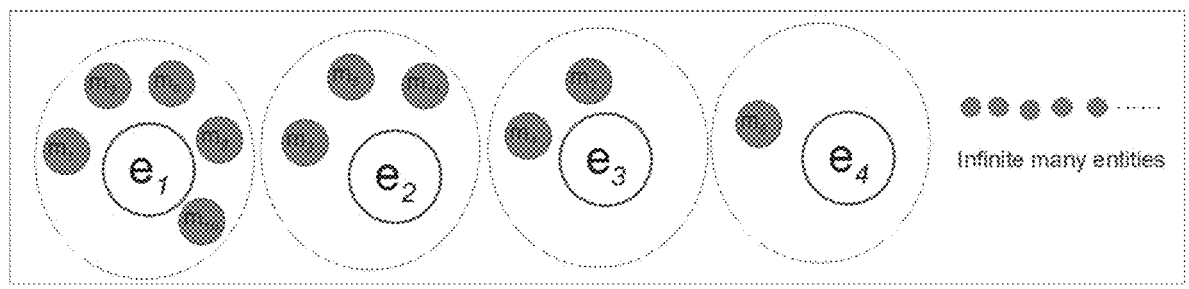
FIG. 9 illustrates an example for entity model establishment using an IMTM technique, according to embodiments.

FIG. 9 illustrates an example 900 for entity model establishment using an IMTM technique, according to embodiments. The example 900 is a graphical illustration of the IMTM technique for NER and ERDs. The IMTM technique can handle an uncertain number of entities given a certain number of mentions. As such, the model may be considered an infinite model rather than a finite model. In particular, in given a document, the IMTM technique can be carried-out without knowing in advance how many coreferring mentions are included. When used with Gibbs sampling, for example, the IMTM technique can generate entities close to the actual ones. Various other possibilities consistent with aspects described herein both explicitly and implicitly are considered.

Figure 10:
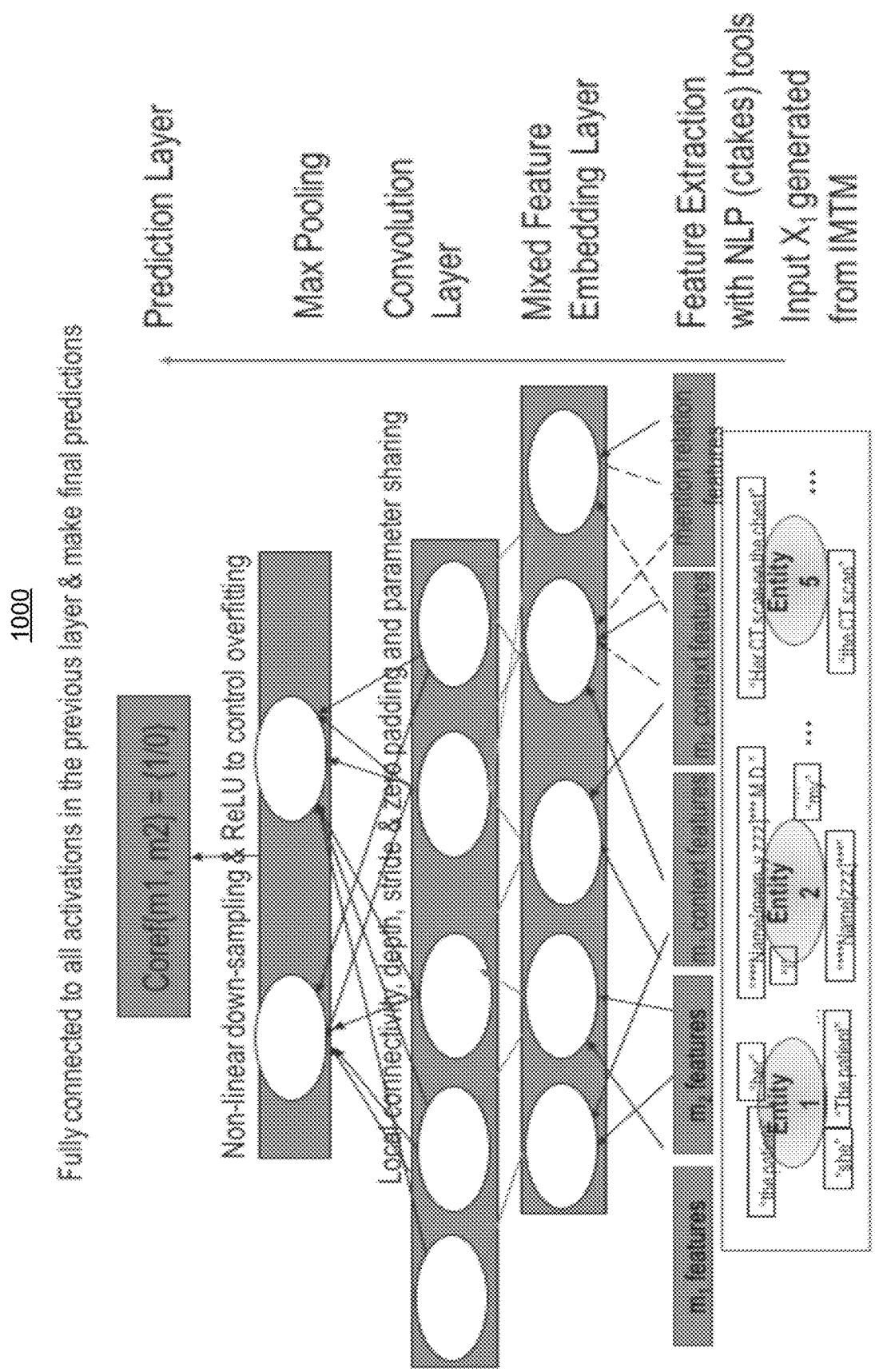
FIG. 10 illustrates an example for entity model establishment using an IMTM technique, according to embodiments.

FIG. 10 illustrates an example 1000 for entity model establishment using an IMTM technique, according to embodiments. The example 1000 may begin by using feature extraction (e.g., with natural language processing). After extracting the features, various combinations and permutations may be mixed in a mixed feature embedding layer. The convolution layer may filter or synthesize the data. The data may then be analyzed with respect to elements such as local connectivity, depth, parameter sharing, etc. Accordingly, items may be sorted into a pair via pooling and a prediction may be provided. Various other possibilities consistent with aspects described herein both explicitly and implicitly are considered.

Figure 11:
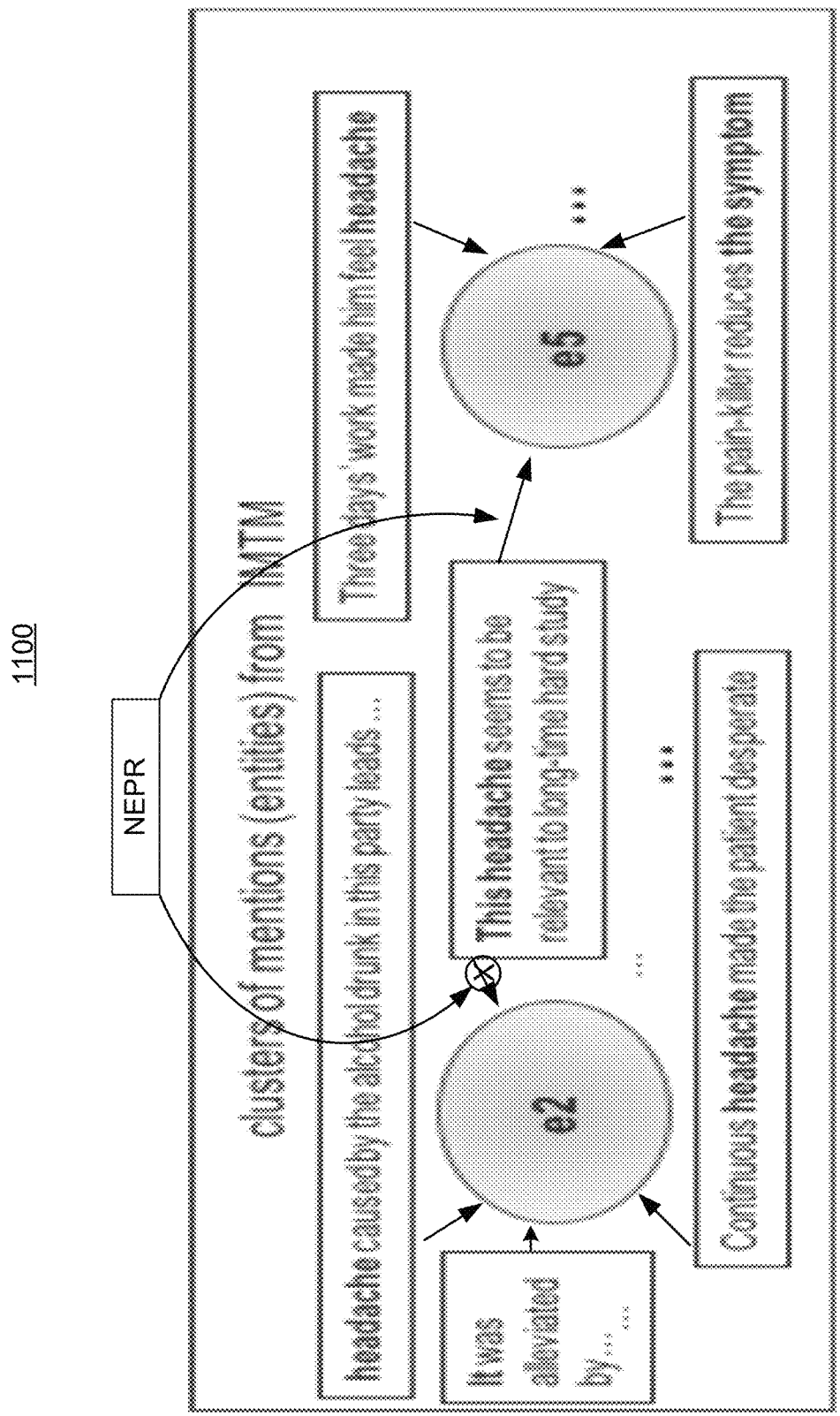
FIG. 11 illustrates an example for entity model establishment using an IMTM technique, according to embodiments.

FIG. 11 illustrates an example 1100 for entity model establishment using an IMTM technique, according to embodiments. The NEPR may further refine NER and ERDs in response to development of the NER and ERDs. The NEPR can account for various contexts of the data using various considerations. For example, mention features from IMTM can indicate that "this headache" is e2. As such, context features from NEPR can correct it to e5 based on the closeness between e2 and e5. Various other possibilities consistent with aspects described herein both explicitly and implicitly are considered.

Altogether, aspects of the disclosure relate to NER and ERD in free texts using an IMTM technique with a neural network. The IMTM technique can construct entity chains among medical events and a NEPR technique to improve performance. In embodiments, the entity chain may include identical entity chains. Features may consider uncertainty of entity data in each document. The dynamicity of the IMTM technique in generating new entities may have positive impacts with respect to the need of pre-estimation of entity numbers. In embodiments, traceable longitudinal electronic health records facilitated by the NER and ERDs may be constructed. Aspects related to a semi-supervised feature may have positive impacts with respect to a level of dependency on training data.

In addition to embodiments described above, other embodiments having fewer operational steps, more operational steps, or different operational steps are contemplated. Also, some embodiments may perform some or all of the above operational steps in a different order. In embodiments, operational steps may be performed in response to other operational steps. The modules are listed and described illustratively according to an embodiment and are not meant to indicate necessity of a particular module or exclusivity of other potential modules (or functions/purposes as applied to a specific module).

In the foregoing, reference is made to various embodiments. It should be understood, however, that this disclosure is not limited to the specifically described embodiments. Instead, any combination of the described features and elements, whether related to different embodiments or not, is contemplated to implement and practice this disclosure. Many modifications and variations may be apparent to those of ordinary skill in the art without departing from the scope and spirit of the described embodiments. Furthermore, although embodiments of this disclosure may achieve advantages over other possible solutions or over the prior art, whether or not a particular advantage is achieved by a given embodiment is not limiting of this disclosure. Thus, the described aspects, features, embodiments, and advantages are merely illustrative and are not considered elements or limitations of the appended claims except where explicitly recited in a claim(s).

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Embodiments according to this disclosure may be provided to end-users through a cloud-computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud-computing resources are provided to a user on a pay-per-use basis, where users are charged only for the computing resources actually used (e.g., an amount of storage space used by a user or a number of virtualized systems instantiated by the user). A user can access any of the resources that reside in the cloud at any time, and from anywhere across the Internet. In context of the present disclosure, a user may access applications or related data available in the cloud. For example, the nodes used to create a stream computing application may be virtual machines hosted by a cloud service provider. Doing so allows a user to access this information from any computing system attached to a network connected to the cloud (e.g., the Internet).

Embodiments of the present disclosure may also be delivered as part of a service engagement with a client corporation, nonprofit organization, government entity, internal organizational structure, or the like. These embodiments may include configuring a computer system to perform, and deploying software, hardware, and web services that implement, some or all of the methods described herein. These embodiments may also include analyzing the client's operations, creating recommendations responsive to the analysis, building systems that implement portions of the recommendations, integrating the systems into existing processes and infrastructure, metering use of the systems, allocating expenses to users of the systems, and billing for use of the systems.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to exemplary embodiments, other and further embodiments of the invention may be devised without departing from the basic scope thereof, and the scope thereof is determined by the claims that follow. The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

The terminology used herein is for the purpose of describing particular embodiments only and is not intended to be limiting of the various embodiments. As used herein, the singular forms "a," "an," and "the" are intended to include the plural forms as well, unless the context clearly indicates otherwise. "Set of," "group of," "bunch of," etc. are intended to include one or more. It will be further understood that the terms "includes" and/or "including," when used in this specification, specify the presence of the stated features, integers, steps, operations, elements, and/or components, but do not preclude the presence or addition of one or more other features, integers, steps, operations, elements, components, and/or groups thereof. In the previous detailed description of exemplary embodiments of the various embodiments, reference was made to the accompanying drawings (where like numbers represent like elements), which form a part hereof, and in which is shown by way of illustration specific exemplary embodiments in which the various embodiments may be practiced. These embodiments were described in sufficient detail to enable those skilled in the art to practice the embodiments, but other embodiments may be used and logical, mechanical, electrical, and other changes may be made without departing from the scope of the various embodiments. In the previous description, numerous specific details were set forth to provide a thorough understanding the various embodiments. But, the various embodiments may be practiced without these specific details. In other instances, well-known circuits, structures, and techniques have not been shown in detail in order not to obscure embodiments.

What is claimed is:

1. A computer-implemented method for entity model establishment using an infinite mixture topic modeling (IMTM) technique with a neural network, the method comprising:

receiving a natural language query via a query module from a user on a personal electronic device by a question analyzer of a question answering system, wherein the question analyzer comprises:
a tokenizer which identifies word boundaries of the natural language query and converts a sequence of characters of the natural language query into a sequence of tokens, analyzes word boundaries and separates the natural language query into component parts comprising words, multiword tokens, numbers and punctuation marks, wherein the sequence of tokens comprises a string of characters of the natural language query categorized as a symbol able to be recognized by the question answering system,
a part of speech tagger which determines a part of speech which a component of the natural language query corresponds to, based on a definition of the component and a context of the component, and
a semantic relationship identifier which determines semantic relationships in the natural language query and grammatical structure of sentences of the natural language query, wherein the question analyzer provides the natural language query in a data structure in a form of a parse tree;
detecting a set of medical event data in an information corpus of the question answering system, using the IMTM technique, which corresponds to a set of medical events corresponding to the natural language query by both a query processor and a visualization processor, both of an answer generator of the question answering system, wherein
the query processor identifies the set of medical event data matching the natural language query, and the visualization processor renders both visualization of the set of medical event data and renders analytics to represent an understandable form to an answer to the natural language query using images, charts, tables, dashboards and maps;

analyzing, using the IMTM technique, the set of medical event data which corresponds to the set of medical events, wherein the IMTM technique constructs entity chains among medical events in an unsupervised fashion and uses a neural entity pair refiner (NEPR) technique in a supervised fashion;

determining, based on analyzing the set of medical event data using the IMTM technique, a set of entity models for the set of medical events;

analyzing, using a neural entity pair refining technique, the set of entity models for the set of medical events based on a set of convolution factors;

establishing, based on the set of entity models for the set of medical events, using the IMTM technique, a subset of the set of entity models for the set of medical events based on the analysis of the set of entity models, wherein at least one subset comprises a single entity model and is established by selecting the at least one subset based on a confidence value of a subset of the set of medical events which comprises image medical events; and providing a natural language result to the user on the personal electronic device based on the received natural language query, the detecting the set of medical of event data, the analyzing the set of medical event data, the determining the set of entity model, the analyzing the set of entity models and the establishing the subset of the set of entity models by the answer generator.

2. The method of claim 1, further comprising:
configuring the set of entity models to include a set of entity chains; and
configuring the subset of the set of entity models to include a subset of the set of entity chains.

3. The method of claim 1, further comprising:
configuring the set of entity models to include a set of identical entity chains; and
configuring the subset of the set of entity models to include a subset of the set of identical entity chains.

4. The method of claim 1, further comprising:
configuring the set of entity models to indicate at least one coreference resolution.

5. The method of claim 1, further comprising:
ingesting, using the IMTM technique, the set of medical event data which corresponds to the set of medical events; and
processing, using the IMTM technique, a certain group of mention elements of the set of medical event data, wherein a respective mention element of the certain group of mention elements correlates to one or more distinct entity elements.

6. The method of claim 1, further comprising:
clustering, using a similarity metric and based on analyzing the set of medical event data using the IMTM technique, the set of medical event data which corresponds to the set of medical events.

7. The method of claim 1, further comprising:
deriving, using a Gibbs sampling technique with respect to the set of medical event data, a set of IMTM parameters for utilization by the IMTM technique.

8. The method of claim 1, further comprising:
extracting, using a natural language processing technique, a set of features, wherein the set of features is both indicated by the set of entity models and derived from the set of medical event data.

9. The method of claim 8, further comprising:
configuring the set of features to include a set of contextual elements.

10. The method of claim 8, further comprising:
analyzing a set of combinations of the set of features; and
computing, with respect to the set of combinations of the set of features, a set of convolution factors.

11. The method of claim 10, further comprising:
resolving, based on the set of convolution factors, the subset of the set of entity models for the set of medical events.

12. The method of claim 1, further comprising:
constructing a set of electronic health record data based on the subset of the set of entity models for the set of medical events.

13. The method of claim 1, further comprising:
configuring the set of medical events to include a set of image events; and
processing a set of image data based on the subset of the set of entity models for the set of image events.

14. The method of claim 1, further comprising:
detecting that the set of medical event data includes both structured data and unstructured data; and
extracting, using a natural language processing technique with respect to the set of medical event data, a set of features for utilization as a set of analysis parameters.

15. The method of claim 1, further comprising:
determining, independent of manual coreference annotation, the set of entity models for the set of medical events; and
establishing, in response to determining the set of entity models for the set of medical events independent of manual coreference annotation, the subset of the set of entity models for the set of medical events.

16. The method of claim 1, further comprising:
executing, in a dynamic fashion to streamline entity model establishment, each of:
the detecting,
the analyzing,
the determining, and
the establishing.

17. The method of claim 1, further comprising:
executing, in an automated fashion without user intervention, each of:
the detecting,
the analyzing,
the determining, and
the establishing.

18. A computer system for entity model establishment using an infinite mixture topic modeling (IMTM) technique with a neural network, the system comprising:
a memory having a set of computer readable computer instructions, and
a processor for executing the set of computer readable instructions, the set of computer readable instructions comprising:
receiving a natural language query via a query module from a user on a personal electronic device by a question analyzer of a question answering system, wherein the question analyzer comprises:
a tokenizer which identifies word boundaries of the natural language query and converts a sequence of characters of the natural language query into a sequence of tokens, analyzes word boundaries and separates the natural language query into component parts comprising words, multiword tokens, numbers and punctuation marks, wherein the sequence of tokens comprises a string of characters of the natural language query categorized as a symbol able to be recognized by the question answering system, a part of speech tagger which determines a part of speech which a component of the natural language query corresponds to, based on a definition of the component and a context of the component, and a semantic relationship identifier which determines semantic relationships in the natural language query and grammatical structure of sentences of the natural language query, wherein the question analyzer provides the natural language query in a data structure in a form of a parse tree;

detecting a set of medical event data in an information corpus of the question answering system, using the IMTM technique, which corresponds to a set of medical events corresponding to the natural language query by both a query processor and a visualization processor, both of an answer generator of the question answering system, wherein the query processor identifies the set of medical event data matching the natural language query, and the visualization processor renders both visualization of the set of medical event data and renders analytics to represent an understandable form to an answer to the natural language query using images, charts, tables, dashboards and maps;

analyzing, using the IMTM technique, the set of medical event data which corresponds to the set of medical events, wherein the IMTM technique constructs entity chains among medical events in an unsupervised fashion and uses a neural entity pair refiner (NEPR) technique in a supervised fashion;

determining, based on analyzing the set of medical event data using the IMTM technique, a set of entity models for the set of medical events;

analyzing, using a neural entity pair refining technique, the set of entity models for the set of medical events based on a set of convolution factors;

establishing, based on the set of entity models for the set of medical events, using the IMTM technique, a subset of the set of entity models for the set of medical events based on the analysis of the set of entity models, wherein at least one subset comprises a single entity model and is established by selecting the at least one subset based on a confidence value of a subset of the set of medical events which comprises image medical events; and providing a natural language result to the user on the personal electronic device based on the received natural language query, the detecting the set of medical of event data, the analyzing the set of medical event data, the determining the set of entity model, the analyzing the set of entity models and the establishing the subset of the set of entity models by the answer generator.

19. A computer program product for entity model establishment using an infinite mixture topic modeling (IMTM) technique with a neural network, the computer program product comprising a computer readable storage medium having program instructions embodied therewith, wherein the computer readable storage medium is not a transitory signal per se, the program instructions executable by a processor to cause the processor to perform a method comprising:

receiving a natural language query via a query module from a user on a personal electronic device by a question analyzer of a question answering system, wherein the question analyzer comprises:

a tokenizer which identifies word boundaries of the natural language query and converts a sequence of characters of the natural language query into a sequence of tokens, analyzes word boundaries and separates the natural language query into component parts comprising words, multiword tokens, numbers and punctuation marks, wherein the sequence of tokens comprises a string of characters of the natural language query categorized as a symbol able to be recognized by the question answering system, a part of speech tagger which determines a part of speech which a component of the natural language query corresponds to, based on a definition of the component and a context of the component, and a semantic relationship identifier which determines semantic relationships in the natural language query and grammatical structure of sentences of the natural language query, wherein the question analyzer provides the natural language query in a data structure in a form of a parse tree;

detecting a set of medical event data in an information corpus of the question answering system, using the IMTM technique, which corresponds to a set of medical events corresponding to the natural language query by both a query processor and a visualization processor, both of an answer generator of the question answering system, wherein the query processor identifies the set of medical event data matching the natural language query, and the visualization processor renders both visualization of the set of medical event data and renders analytics to represent an understandable form to an answer to the natural language query using images, charts, tables, dashboards and maps;

analyzing, using the IMTM technique, the set of medical event data which corresponds to the set of medical events, wherein the IMTM technique constructs entity chains among medical events in an unsupervised fashion and uses a neural entity pair refiner (NEPR) technique in a supervised fashion;

determining, based on analyzing the set of medical event data using the IMTM technique, a set of entity models for the set of medical events;

analyzing, using a neural entity pair refining technique, the set of entity models for the set of medical events based on a set of convolution factors;

establishing, based on the set of entity models for the set of medical events, using the IMTM technique, a subset of the set of entity models for the set of medical events based on the analysis of the set of entity models, wherein at least one subset comprises a single entity model and is established by selecting the at least one subset based on a confidence value of a subset of the set of medical events which comprises image medical events; and providing a natural language result to the user on the personal electronic device based on the received natural language query, the detecting the set of medical of event data, the analyzing the set of medical event data, the determining the set of entity model, the analyzing the set of entity models and the establishing the subset of the set of entity models by the answer generator.

* * * * *